US00PP34953P2

(12) United States Plant Patent
Verhoef

(10) Patent No.: US PP34,953 P2
(45) Date of Patent: Jan. 31, 2023

(54) ***WEIGELA* PLANT NAMED 'VBL1'**

(50) Latin Name: *Weigela florida*
Varietal Denomination: VBL1

(71) Applicant: Gijsbertus Verhoef, Hazerswoude-Dorp (NL)

(72) Inventor: Gijsbertus Verhoef, Hazerswoude-Dorp (NL)

(73) Assignee: BERT VERHOEF BOOMKWEKERIJ B.V., Hazerswoude-Dorp (NL)

( * ) Notice: Subject to any disclaimer, the term of this patent is extended or adjusted under 35 U.S.C. 154(b) by 0 days.

(21) Appl. No.: 17/738,437

(22) Filed: May 6, 2022

(30) Foreign Application Priority Data

Jul. 27, 2021 (CA) ..... PBR 21-10648

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Penny J. Aguirre

(57) ABSTRACT

A new cultivar of *Weigela florida* plant named 'VBL1' that is characterized by its compact plant habit, its young foliage that is brown in color and mature foliage that is brown-green in color, its floriferous blooming habit that is moderately remontant; blooming in May with a second blooming period in August and September, and its flowers that are red-purple in color.

2 Drawing Sheets

Botanical classification: *Weigela florida.*
Variety denomination: 'VBL1'.

CROSS REFERENCE TO A RELATED APPLICATION

This application claims priority to a Canadian Plant Breeder's Rights Application No. 21-10648 filed on Jul. 27, 2021, under 35 U.S.C. 119(f), the entire contents of which is incorporated by reference herein.

BACKGROUND OF THE INVENTION

The present invention relates to a new and distinct cultivar of *Weigela* and will be referred to hereafter by its cultivar name, 'VBL1'. 'VBL1' represents a new cultivar of *Weigela*, a deciduous shrub grown for landscape use.

The new cultivar is the result of a controlled breeding program conducted by the Inventor in Hazerswoude-Dorp, The Netherlands. The goal of the breeder program is to develop new cultivars of *Weigela* that are floriferous with multi-colored flowers and compact plant habits. The Inventor made a cross in spring of 2013 between *Weigela* 'Verweig 3' (not patented) as the female parent and *Weigela* 'Velda' (U.S. Plant Pat. No. 26,842) as the male parent. 'VBL1' was selected as a single unique plant from the resulting seedlings of the cross in spring of 2018.

Asexual propagation of the new cultivar was first accomplished by softwood stem cuttings by the Inventor in July of 2017 in Hazerswoude-Dorp, The Netherlands. Asexual propagation by softwood stem cuttings has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'VBL1' as a unique cultivar of *Weigela.*

1. 'VBL1' exhibits a compact plant habit.
2. 'VBL1' exhibits young foliage that is brown in color and mature foliage that is brown-green in color.
3. 'VBL1' exhibits a floriferous blooming habit that is moderately remontant; blooming in May with a second blooming period in August and September.
4. 'VBL1' exhibits flowers that are red-purple in color.

The female parent plant differs from 'VBL1' in having a lower and broader spreading plant habit and foliage that is much darker brown to purple-brown in color. The male parent plant differs from 'VBL1' in having foliage that is much darker brown to black-brown in color and flowers that are white in color. 'VBL1' can be compared to the *Weigela florida* varieties 'Alexandra' (U.S. Plant Pat. No. 10,772) and 'Samba' (not patented). 'Alexandra' is similar to 'VBL1' in having dark colored foliage and flowers that are red-purple in color. 'Alexandra' differs from 'VBL1' in having a much less compact plant habit and a less floriferous blooming habit with no reblooming. 'Samba' is similar to 'VBL1' in having dark foliage and a compact plant habit. 'Samba' differs from 'VBL1' in having a more compact plant habit, a shorter plant height, foliage that is lighter brown to purple-brown in color, and flowers that are more purple in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales that fall within a one-year grace period to the filing date. Disclosures include website listings by Wilson's Garden Center, North Carolina Extension Gardener, Garden Design, Monrovia, Proven Winners, and Pahls.

BRIEF DESCRIPTION OF THE DRAWINGS

The accompanying color photographs illustrates the overall appearance and distinct characteristics of a 17-month-old plant of the new cultivar as grown outdoors in a 2-gallon container in Abbotsford, British Columbia, Canada.

The photograph in FIG. 1 provides a side view of 'VBL1' in bloom.

Figure 1:
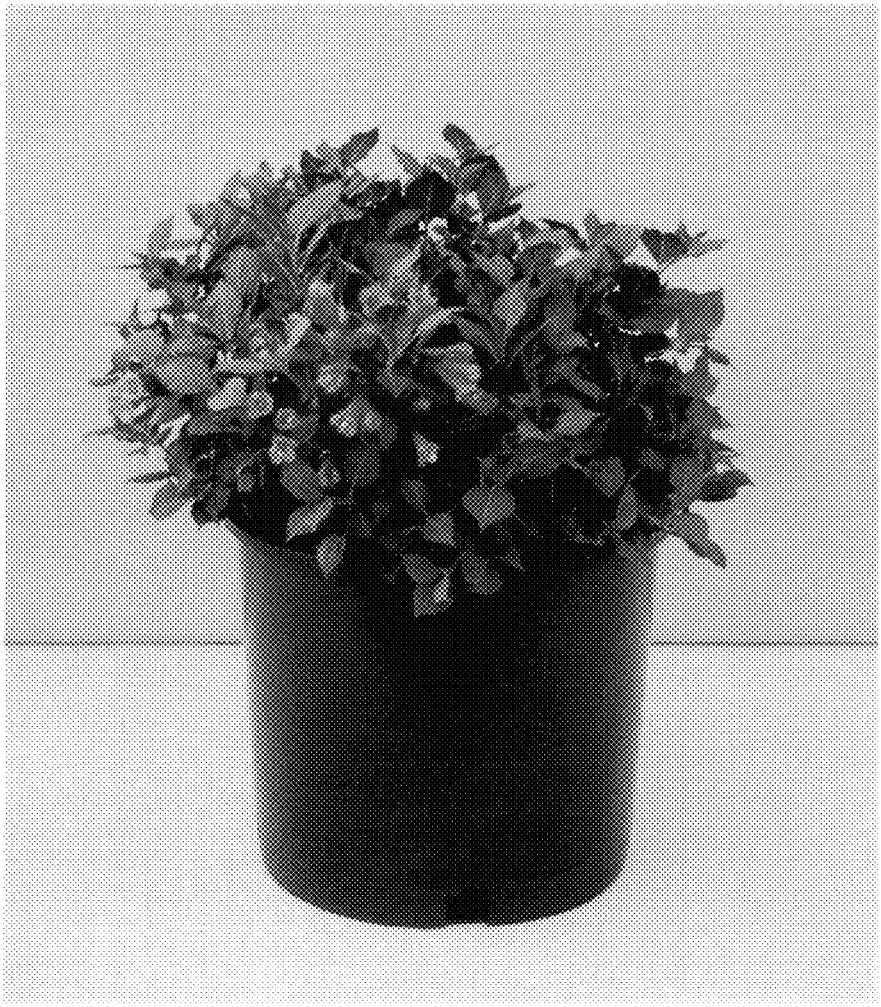
Figure 2:
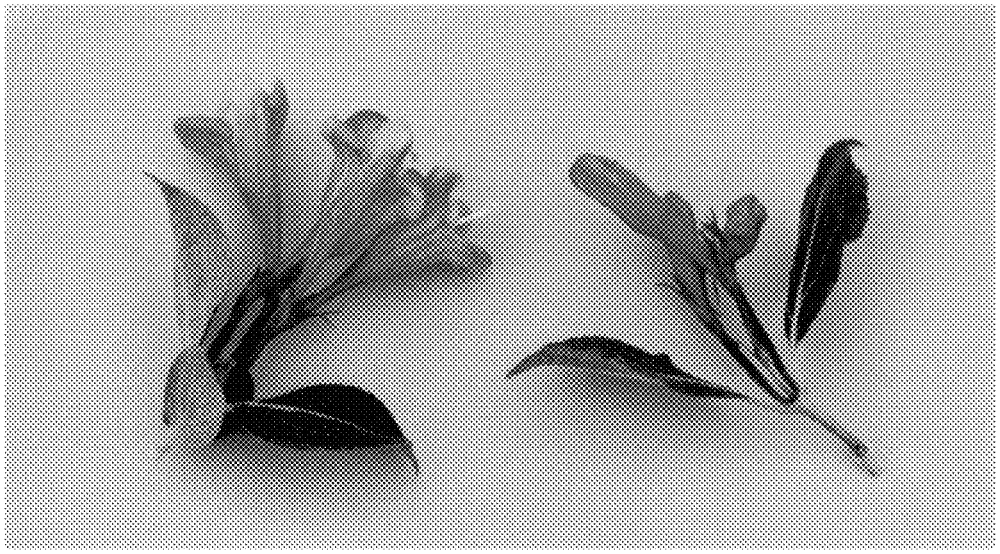

The photograph in FIG. 2 provides a close-up view of the flowers of 'VBL1'.

The colors in the photograph may differ slightly from the color values cited in the detailed botanical description, which accurately describe the colors of the new *Weigela*.

DETAILED BOTANICAL DESCRIPTION

The following is a detailed description of 17-month-old plants of the new cultivar as grown outdoors in 2-gallon containers in Abbotsford, British Columbia, Canada. Phenotypic differences may be observed with variations in environmental, climatic, and cultural conditions. The color determination is in accordance with The 2015 Colour Chart of The Royal Horticultural Society, London, England, except where general color terms of ordinary dictionary significance are used.

General description:

*Blooming period*.—Blooms in spring (May) and repeats during summer and fall in Canada.

*Plant type*.—Deciduous shrub.

*Plant habit*.—Broadly mounded, freely branched.

*Plant size*.—In the landscape; an average of 33.0 cm in height (soil level to top of floral plane) and 72.5 cm in diameter, eventually a mature plant will be 60 cm in height and width.

*Hardiness*.—At least in U.S.D.A. Zones 4 to 7.

*Diseases and pests*.—No susceptibility or resistance to diseases or pests has been observed.

*Root description*.—Fibrous, moderately dense.

*Propagation*.—Softwood stem cuttings.

*Root initiation*.—About 3 weeks.

*Root development*.—An average of 3 months to produce a young rooted plant from a rooted cutting.

*Growth rate*.—Moderately vigorous.

Branch description:

*Branch shape*.—Rounded.

*Branch color*.—New growth; 145B, mature wood; bark; 199B and 199D.

*Lenticels*.—Numerous; 1.5 mm, 158C in color.

*Branch size*.—An average of 24.7 cm in length and 4 mm in diameter.

*Branch surface*.—Weaky glossy, very sparsely pubescent with short strigose hairs, bark; rough texture.

*Branch aspect*.—Upright to outward at an average angle of 40°.

*Branch quantity*.—Average of 4 main branches, 8 lateral branches with an average of 30 branchlets.

*Internode length*.—2.9 cm.

Foliage description:

*Leaf shape*.—Obovate.

*Leaf division*.—Simple.

*Leaf base*.—Cuneate.

*Leaf apex*.—Apiculate.

*Leaf fragrance*.—None.

*Leaf aspect*.—Held in an average angle of 40° to lateral branch.

*Leaf venation*.—Pinnate, color upper surface; 144B with N186C around the edges on new growth, color lower surface; 144B with N186C on secondary veins and 144C on mature growth, color lower surface; 145D.

*Leaf margins*.—Serrate.

*Leaf arrangement*.—Opposite.

*Leaf attachment*.—Petiolate.

*Leaf surface*.—Both surfaces are smooth, glabrous with slight glossiness, slightly rugose, mid-vein covered with dense pubescence, lateral veins moderately pubescent with hairs an average of 0.1 mm in length and 155A in color.

*Leaf size*.—An average of 7.5 cm in length and 4.4 cm in width.

*Leaf quantity*.—An average of 28 (14 pairs) per lateral branch.

*Leaf color*.—Young upper surface; closest to 200A, base 183A, young lower surface; 146B, margins and top 176A, mature and fall upper surface; NN137A, moderately tinged with 200A, mature and fall lower surface; 147B.

*Petioles*.—Average of 8.4 mm in length, 1 mm in width, flattened, upper surface color 144C, lower surface color 145C, strong, both surfaces are smooth and slightly glossy with margins covered with short soft hairs an average of 0.5 mm in length and 156D in color.

*Stipules*.—None.

Inflorescence description:

*Inflorescence type*.—Solitary, in pairs, or in small clusters at terminus and leaf axils.

*Inflorescence size*.—An average of 6.1 cm in height (including peduncle), 5.2 cm in diameter.

*Flower buds*.—Oblanceolate in shape, an average of 2.8 cm in depth and 8 mm in diameter, 58A in color, smooth, glabrous and matte surface, very sparsely covered with very short hairs; an average of 0.2 mm in length and too small to measure color.

*Flower fragrance*.—None.

*Lastingness of flowers*.—About 12 days, self-cleaning.

*Flower aspect*.—Outward to slightly upright.

*Flower quantity*.—An average 2 to 4 per inflorescence, 125 buds and flowers per plant.

*Flower type*.—Tubular.

*Flower size*.—Average of 1.2 cm in height, 1 cm in diameter, flower lobe; 8 mm in length, 7 mm in width, tube; 1.5 cm in length, 2 mm in diameter.

*Peduncles*.—Average of 1 cm in length and 1.3 mm in diameter, held straight on top of lateral branch, rounded, moderate strength, moderately pubescent, 144B in color and tinged with 187A.

*Calyx*.—Rotate in shape, an average of 1 cm in depth and 1 cm in width.

*Sepals*.—5, rotate, linear in shape, narrowly acute apex, cuneate base, lower 50% fused, entire margin, an average of 6 mm in length and 0.5 mm in width, upper and lower surface is smooth, sparsely pubescent and dull, color; when opening upper and lower surface N200B to N200C, base 185A, tip 146D, when fully open upper and lower surface N200B, base 187A.

*Petals.*—5, lower 75% fused into tube, spathulate in shape, margin entire on free portion, apex obtuse, an average of 8 mm in length, 7 mm in width, upper and lower surface glabrous and moderately velvety, color; fully open upper surface; N74C to N74D, fully open lower surface N74C to N74D, and 59D, throat color; 186A to 186B and 59D, inner surface 75C to N74C with a narrow elliptic shaped marking of 8A and 10A to 10B, tube color; 59D and 186B.

Reproductive organs:

*Gynoecium.*—Pistil; 1, average of 3.2 cm in length, style; average of 1.45 cm in length, and 154D in color, with 63C in color at proximal end, stigma; club-shaped, 1.5 mm in length, 2 mm in diameter, 154C in color, ovary; inferior, 1.7 cm in length, 1.4 mm in diameter; 200A in color with 197A at base.

*Androecium.*—Stamens; 5, filaments; N155B flecked with 186C in color and an average of 1 cm in length, implanted in petals, anthers; 155A in color, an average of 4 mm in length, 0.5 mm in width, narrowly oblong in shape, pollen; moderate in quantity and 11D in color.

*Fruit and seed.*—No fruit or seed production has been observed to date.

It is claimed:

1. A new and distinct cultivar of *Weigela* plant named 'VBL1' as herein illustrated and described.

* * * * *